United States Patent [19]

Sasaki et al.

[11] Patent Number: 5,350,782
[45] Date of Patent: Sep. 27, 1994

[54] DENTAL FILLING COMPOSITION

[75] Inventors: Hiroyuki Sasaki, Osaka; Tetsuro Ota, Kyoto; Eiji Hattori, Kanagawa; Michihiro Ikeda, Fukuoka, all of Japan

[73] Assignees: Kanebo, Ltd.; Mitsubishi Kasei Corporation, both of Tokyo, Japan

[21] Appl. No.: 940,458

[22] Filed: Sep. 4, 1992

[30] Foreign Application Priority Data

Sep. 6, 1991 [JP] Japan .................. 3-255673

[51] Int. Cl.$^5$ .................. A61K 6/08; C08K 3/18; C08K 3/22
[52] U.S. Cl. .................... 523/116; 524/430
[58] Field of Search .............. 523/116; 524/493, 430

[56] References Cited

U.S. PATENT DOCUMENTS 4,163,004  7/1979  Erickson et al. ............. 523/116
4,407,984  10/1983  Ratcliffe et al. ............. 524/493

FOREIGN PATENT DOCUMENTS 2002017  of 0000  Canada .
2051333  of 0000  Canada .
0368657A2  of 0000  European Pat. Off. .
0475239A2  of 0000  European Pat. Off. .

*Primary Examiner*—Paul R. Michl
*Assistant Examiner*—LaVonda R. DeWitt
*Attorney, Agent, or Firm*—Kane, Dalismer, Sullivan, Kurucz, Levy, Eisele and Richard

[57] ABSTRACT

A dental filling composition comprising a polymerizable monomer and an inorganic filler, characterized in that the inorganic filler comprises (A) 20 to 80% by weight of spherical inorganic oxide particles with an average particle size of from 1.0 to 5.0 μm, and (B) 80 to 20% by weight of spherical inorganic oxide particles which have a particle size range of at least 0.05 μm and less than 1.0 μm and at least 5% by weight of which is in a particle size range of from 0.05 to 0.2 μm. The dental filling composition may have a high content of the inorganic filler and, upon curing, has good mechanical strength, good surface glass and smoothness, low water absorption, and transparency compared to that of natural teeth, in which smaller particles are sufficiently packed in interstices among larger particles, and smaller particles serve also for the good transparency.

3 Claims, No Drawings

DENTAL FILLING COMPOSITION

FIELD OF THE INVENTION

The present invention relates to a dental filling composition comprising a polymerizable monomer and an inorganic filler, more specifically a dental filling composition in which a content of an inorganic filler is high and which, upon curing, has excellent surface gloss and smoothness, and mechanical strength, and transparency comparable to that of natural teeth.

PRIOR ART

Dental filling compositions comprising polymerizable monomers and inorganic fillers were used to repair teeth damaged by dental caries, etc. It was also tried to apply such dental filling compositions in inlays and crowns.

Various combinations of acrylic monomers with inorganic fillers such as silica or various glass powder were proposed as a dental filling composition. Performance of a dental filling composition depends much upon composition, shape, particle size, particle size distribution and content of the inorganic filler.

A filling composition proposed in an early period contained an inorganic powdery filler with a particle size of 5 to 100 $\mu$m. This composition has a large content of the filler and, upon polymerization curing, excellent mechanical strength. However, smoothness of the cured surface is insufficient due to the large particles present. Even after finish polishing, the polished surface feels rough and seems less bright. Then, crushed natural silica in which large particles were removed to adjust the largest particle size below 10 $\mu$m was used, and smoothness of the surface was surely improved, but gloss was still insufficient, a content of the filler was at most 70 to 80% by weight, and mechanical strength was unsatisfactory yet.

Accordingly, in order to attain improved smoothness on the cured surface, a method was proposed where synthesized ultra-fine silica with a particle size range of 0.01 to 0.03 $\mu$m was used as an inorganic filler. However, the ultra-fine silica has an extremely large specific surface area and, therefore, its content is so small as: 40 to 50% by weight, resulting in high water absorption and high heat expansion of a cured product.

In order to solve the aforesaid problems, a hybrid type of inorganic filler was proposed which comprised crushed natural silica with a regulated particle size of 10 $\mu$m or less and ultra-fine silica together (Japanese Patent Application Laid-Open Sho-63-88110/1988). A high content of a filler and almost sufficient mechanical strength are attained with this filler, but smoothness of the cured surface is poor and its gloss is not sufficient, either.

A dental filling composition was proposed which contained synthesized spherical silica having a narrow particle size distribution with a particle size range of from 0.1 to 1.0 $\mu$m (Japanese Patent Application Laid-Open Sho-58-41810/1983). However, even with the above spherical silica, a filler content is only approximately 75% by weight, and the cured composition is low in mechanical strength such as bending strength and Knoop hardness number. It was also proposed that mechanical strength was improved by the use of at least two groups of spherical inorganic oxide particles having different average particle sizes and being, however, in a particle size range of 0.1 to 1.0 $\mu$m (Japanese Patent Application Laid-Open Sho-58-152804/1983). Some improvement on mechanical strength is surely seen. However, the mixture of these small particles has a large specific surface area and, therefore, the cured composition has a bending strength of only 900 kg/cm$^2$ and a filler content of 80 wt. % at most, which are insufficient for a dental filling composition.

A dental composite composition was proposed, in which a filler comprised particles of an average size of 1.0 to 100 $\mu$m and particles having a narrow particle size distribution with a particle size range of 0.1 to 1.0 $\mu$m. It is said that the composition has so good flowability as to quickly penetrate into dentinal tubuli to yield a high content of the filler in the tubuli (Japanese Patent Application Laid-Open Sho-61-148109/1986). Thus, the main purpose of that invention is good flowability to attain a high filler content in tubuli. No mention is made on improvement of surface smoothness or mechanical strength. In fact, the bending strength is so small as 1,000 kg/cm$^2$ at most. It is believed that its surface smoothness is insufficient just as in the aforesaid hybrid type one, due to the existence of the larger particles, e.g., particles of an average size of 5 to 18 $\mu$m in the Examples.

Besides, a composition comprising synthesized silica and acrylic monomers has many advantages such as stable availability of the raw materials, high mechanical strength after cured and good stability with time of the composition, but a refraction index of the synthesized silica differs much from that of acrylic polymers and, therefore, a cured composition has low transparency. It was difficult to attain transparency comparable to that of natural teeth without ultra-fine silica.

As stated above, a dental filling composition has not yet been obtained which, upon curing, has well-balanced properties, that is, mechanical strength, smoothness and gloss of the surface and transparency comparable to that of natural teeth.

SUMMARY OF THE INVENTION

The present inventors have now found that such a composition as mentioned just above may be attained by the use of a mixture of spherical inorganic oxides having particular particle sizes.

The present invention provides a dental filling composition comprising a polymerizable monomer and an inorganic filler, characterized in that the inorganic filler comprises (A) 20 to 80% by weight of spherical inorganic oxide particles with an average particle size of from 1.0 to 5.0 $\mu$m, and (B) 80 to 20% by weight of spherical inorganic oxide particles which have a particle size range of at least 0.05 $\mu$m and less than 1.0 $\mu$m and at least 5% by weight of which is in a particle size range of from 0.05 to 0.2 $\mu$m.

PREFERRED EMBODIMENT OF THE INVENTION

Any polymerizable monomers may be used in the invention as far as they can be used in a dental filling composition. Polymerizable vinyl monomers are preferred, such as those having acrylic and/or methacrylic groups. More specifically, these include esters of α-cyanoacrylic acid, (meth)acrylic acid, urethane (meth)acrylic acid, crotonic acid, cinnamic acid, sorbic acid, maleic acid and iraconic acid with mono- or di- hydric alcohols; (meth)acryl amides such as N-isobutyl acrylamide; vinyl esters of carboxylic acids such as vinyl acetate; vinyl ethers such as butyl vinyl ether; mono-N-vinyl compounds such as N-vinyl pyrrolidone; and styrene and its derivatives. Particularly preferred are monofunctional or polyfunctional (meth)acrylic esters and urethane (meth)acrylic esters as stated below.

(a) Monofunctional (meth)acrylic esters

Methyl (meth) acrylate, n- or i- propyl (meth) acrylate, n-, i- or tert. - butyl (meth)acrylate, and 2-hydroxyethyl (meth)arylate.

(b) Difunctional (meth)acrylic esters

Compounds represented by the general formula:

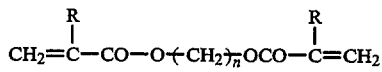

wherein R represents a hydrogen atom or a methyl group, and n is an integer of from 3 to 20, such as di(meth)acrylates of propanediol, butanediol, hexanediol, octanediol, nonanediol, decanediol and eicosanediol; compounds represented by the general formula:

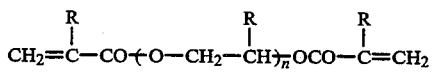

wherein R represents a hydrogen atom or a methyl group, and n is an integer of from 1 to 14, such as di(meth)acrylates of ethylene glycol, diethylene glycol, triethylene glycol, tetraethylene glycol, dodecaethylene glycol, tetradecaethylene glycol, propylene glycol, dipropylene glycol and tetradecapropylene glycol; and glycerin di(meth)acrylate, 2,2'-bis[p-($\gamma$-methacryloxy-$\beta$-hydroxypropoxy)phenyl propane] or Bis-GMA, hisphenol A dimethacrylate, neopentylglycol di(meth)acrylate, 2,2'-di(4-methacryloxy polyethoxyphenyl)propane having 2 to 10 ethoxy groups per molecule and 1,2-bis(3-methacryloxy-2-hydroxypropoxy)butane.

(c) Tri- or more functional (meth)acrylic esters

Trimethylolpropane tri(meth)acrylate and pentaerythritol tetra(meth)acrylate.

(d) Urethane (meth)acrylic esters

Reaction products of two moles of (meth)arylate monomer having a hydroxy group with one mole of diisocyanate, and reaction products of a urethane prepolymer having two NCO end groups with a (meth)acrylate monomer having a hydroxy group, such as those represented by the general formula:
wherein $R_1$ represents a hydrogen atom or a methyl Group, $R_2$ represents an alkylene Group and $R_3$ represent an organic radical.

These vinyl monomers may be used alone or as their mixture as needed. A polymerization initiator may be contained in the present composition as needed. Any known polymerization initiators may be used. Polymerization may be promoted by camphorquinone and light energy, or a combination of peroxide with a promotor.

The other essential component in the present dental filling composition is an inorganic filler which comprises (A) 20 to 80% by weight of spherical inorganic oxide particles with an average particle size of from 1.0 to 5.0 $\mu$m, and (B) 80 to 20% by weight of spherical inorganic oxide particles which has a particle size range of at least 0.05 $\mu$m and less than 1.0 $\mu$m and at least 5% by weight of which has a particle size range of from 0.05 to 0.2 $\mu$m.

In the present invention, the particle size is determined by measuring diameters of particles in a unit area on a photograph of a scanning electron microscope. The average particle size is a number-averaged diameter.

On account of the use of a mixture of those particles, it is possible to attain a dental filling composition which has a high content of an inorganic filler, excellent gloss, smoothness and mechanical strength as well as transparency comparable to that of natural teeth.

The spherical inorganic oxide particles may preferably be of inorganic oxides such as silica, zirconia, alumina and titania, or multi-component inorganic oxides comprising at least one metal component selected from the group consisting of Groups I, II, III and IV of the short form periodic table and silicon. The inorganic oxide particles may be of one kind of oxide or a mixture of two or more kinds of oxides. Particles (A) may be of inorganic oxide different from that of particles (B). Silica and multi-component inorganic oxides comprising silicon and a metallic component are preferred because of their properties suitable to a dental filling composition, availability of their raw materials and easiness of the preparation of their spherical particles. Spherical particles of amorphous silica may be prepared with most ease. Particularly preferred is spherical silica synthesized by hydrolytic polymerization of alkoxy silane. Such amorphous silica is preferably calcined at 500° C. or higher after drying. Alternatively, multi-component inorganic oxides comprising silicon and a metallic component may be chosen because of easier X ray inspection due to the added component of larger specific gravity.

Inorganic oxide particles (A) used in the invention has an average particle size of 1.0 to 5.0 $\mu$m, preferably 1.0 to 3.0 $\mu$m. If it exceeds 5.0 $\mu$m, gloss and smoothness of the cured surface are poor. Meanwhile, if it is less than 1.0 $\mu$m, the difference in particle size from particles (B) is too small to attain a high content of the inorganic filler in a dental filling composition, so that the composition after cured will show low mechanical strength and large water absorption, though gloss and smoothness of the cured surface are good. Further, it is advantageous for better gloss and smoothness of the surface and a higher content of the inorganic filler that inorganic oxide particles (A) have uniform particle sizes, that is, a small standard deviation in a particle size distribution. The coefficient of standard deviation of particles (A) is preferably 0.5 or less. Difference between the sizes of particles (A) and (B) is preferably large, because it is believed that inorganic oxide particles (B), which have a smaller size, are sufficiently packed in interstices among inorganic oxide particles (A), which have a larger size, so that a high content of the inorganic fillers is attained in the invention.

The particle size of inorganic oxide particles (B) ranges substantially from 0.05 to 1.0 $\mu$m, preferably 0.05 to 0.5 $\mu$m, in order that particles (B) are sufficiently packed in interstices among particles (A) to yield a high content of the inorganic filler as stated above. If the particle size of particles (B) is less than 0.05 $\mu$m, the specific surface area is larger and, therefore, the content of the inorganic filler is rather smaller, which results in lower mechanical strength despite one of the purposes of the invention. It is also essential in the invention that at least 5% by weight, preferably 20 to 70% by weight, more preferably 20 to 50% by weight, of inorganic oxide particles (B) has a particle size of 0.05 to 0.2 $\mu$m which is less than half the wave length of visible light (about 0.4 to 0.7 μm). If a too small amount of the inorganic oxide particles (B) have the particle size of 0.05 to 0.2 μm, transmission of visible light through the cured dental filling composition tends to decrease and it is impossible to attain the envisaged transparency comparable to natural teeth. Meanwhile, if a too large amount of the inorganic oxide particles (B) have the particle size of 0.05 to 0.2 μm, a content of the inorganic filler tends to decrease. When a difference between the particle size of the particles which are in a range of from 0.05 to 0.2 μm (B-1) and the particle size of the particles which are larger than 0.2 μm (B-2) is large, particles (B-1) are well packed in interstices among particles (B-2), so that a higher content of the inorganic filler can be attained, as mentioned above about the relation between particles (A) and (B). It is preferred that the average particle size of particles (B-2) is at least twice as large as that of particles (B-1).

Inorganic oxide particles (A) and (B) of the invention are spherical, which leads to a high content of the inorganic filler and gloss and smoothness of the cured dental filing composition. The term "spherical" means really spherical particles as well as substantially spherical particles, such as somewhat oval ones.

The amount of inorganic oxide particles (A) is 20 to 80% by weight, preferably 50 to 75% by weight, based on the total weight of particles (A) and (B). If it is less than 20% by weight, the content of the inorganic filler is too small. If it exceeds 80% by weight, the cured composition is unsatisfactory, for instance, in transparency. The amount of inorganic oxide particles (B) is 20 to 80% by weight, preferably 25 to 50% by weight, based on the total weight of particles (A) and (B). If it exceeds 80% by weight, the specific surface area of particles (B) is too large, so that the content of the inorganic filler is low and mechanical strength is insufficient. If it is less than 20% by weight, the cured composition scatters visible light so much that transparency comparable to that of natural teeth is not attained.

As far as the effects of the invention are not retarded, some other inorganic filler such as ultra-fine silica with a particle size of 0.01 to 0.03 μm or nonspherical inorganic particles may be added, preferably, in an amount of at most 10% by weight based on the total weight of particles (A) and (B).

Inorganic oxide particles (A) and (B) of the invention may separately be admixed with the polymerizable monomer to prepare the dental filling composition. However, it is preferred for a higher content of the inorganic filler that inorganic oxide particles (A) and (B) are mixed with each other in advance of mixing with the polymerizable monomer. This advance mixing of the inorganic oxide particles may be conducted in wet mixing or dry mixing or any other manners. Efficient wet mixing methods include mixing in a polar solvent, such as water, alcohols such as methanol, ethanol and isopropanol, glycols such as ethylene glycol and propylene glycol, dimethylformamide or dimethylsulfoxide. In dry mixing methods, conventional pneumatic mixers, fluid mixers, V mixers, ribbon mixers, screw mixers and disc mixers may be used. Among pneumatic mixers in which particles are mixed in an air flow, particularly preferred are jet mills, air blenders and jet-o-mizers. It is not completely clear why the advance mixing of the particles gives a higher content of the inorganic filler, but it is believed that the mixed particles have such size distribution that smaller particles are easily packed in interstices among larger particles.

The inorganic filler of the invention is preferably surface-treated in advance for better dispersion and mixing in the polymerizable monomer. When the inorganic filler is silica, preferred surface-treating agents include organic silicon compound surface-treating agents, such as γ-methacryloxypropyl trimethoxysilane, vinyl triethoxysilane, vinyl trichlorosilane, vinyl trimethoxysilane, vinyl triacetoxysilane and vinyl tri(methoxyethoxy)silane. Conventional surface treating methods may be used.

The inorganic filler is mixed and kneaded with the polymerizable monomer to prepare the dental filling composition in any conventional manner. For better mechanical strength, the amount of the inorganic filler is at least 80% by weight based on the whole filling composition.

The present composition may contain any other additives such as polymerization inhibitors, colorants and UV absorbers, as needed.

The present invention will be further explained in reference to the following unlimitative examples.

EXAMPLES

Inorganic Filler

In the following Examples and Comparison Examples, various spherical silica particles which were synthesized by hydrolytic polymerization of alkoxysilane and available from Mitsubishi Kasei Corporation, Japan, were used as an inorganic filler.

The silica particles were surface treated as follows. To the silica particles was added 4% by weight, based on the silica particles, of γ-methacryloxypropyl trimethoxysilane (available from Shin-etsu Chemical Company) dissolved in a water/ethanol solvent, stirred and dried at 80° C. for 2 hours and then at 105° C. for 5 hours in a hot air drier.

Polymerizable Monomer

A monomer mixture was prepared by mixing dimethacryloxyethyl trimethylhexamethylene diurethane (trade mark UDMA, Shin Nakamura Kagaku Company) with triethyleneglycol dimethacrylate (TEGDMA, Shin Nakamura Kagaku Company) in a weight ratio of 7 to 3, to which 0.5% by weight of camphorquinone (Aldrich) as a photo sensitizer and 0.5% by weight, based on the monomers, of N,N-dimethylaminoethyl methacrylate (Tokyo Kasei Company) as a reducing agent were then added.

Preparation of Test Pieces and Determination of Properties

1. Compressive strength

A filling composition was filled in a hole of 3 mm in inner diameter and 6 mm in height in a stainless steel mold; the upper and lower ends were pressed with glass plates, which were then irradiated by a visible light irradiator, Econolight available from Yoshida Company, for 40 seconds; and the cured composition was released from the mold. The test piece thus prepared was immediately immersed in water at 37° C. for 24 hours before used in the subsequent test.

Compressive strength was measured with an Instron testing machine, Model 4206, at a cross-head speed of 2 mm/min.

2. Bending strength

A filling composition was filled in a cavity of 2 mm thickness, 2 mm width and 25 mm length in a stainless steel mold; the upper and lower ends in the direction of thickness were pressed with glass plates, which were then irradiated by a photo polymerizer for dental prosthetics, Light Ace available from Yoshida Company, for 120 seconds; and the cured composition was released from the mold. The test piece thus prepared was immediately immersed in water at 37° C. for 24 hours before used in the subsequent test.

Bending strength was measured with an Instron testing machine, Model 4206, at a cross-head speed of 0.5 mm/min.

3. Knoop hardness number

A filling composition was filled in a hole of 20 mm in inner diameter and 2 mm in height in a stainless steel mold; the upper and lower ends were pressed with glass plates, which was then polymerized as in the above 2. The surfaces of the test piece which had been pressed with the glass plates were polished with SiC polishing paper of No. 1500 to prepare for measurement. The test piece thus prepared was immediately immersed in water at 37° C. for 24 hours before used in the subsequent test.

Knoop hardness number was determined with a Knoop hardness number meter (MVK-E, Akashi Seisakusho Company) at a load of 50 g and a load retention time of 20 seconds.

4. Water absorption

A filling composition was filled in a cavity of 3 mm thickness, 15 mm width and 20 mm length in a stainless steel mold, and the upper and lower faces in the direction of thickness were pressed with glass plates, followed by polymerization as in the above 2. Every face of the test piece was polished with SiC polishing paper of No. 240.

The test piece was conditioned in air at 37° C. After its weight became constant, which is referred to as m1, it was immersed in water at 37° C. After 24 hours, it was weighed, say m2. Water absorption is defined as follows:

Water absorption=(m2-m1)/surface area of the test piece.

5. Transparency

A filling composition was filled in a hole of 20 mm in inner diameter and 1 mm in height in a stainless steel mold, and the upper and lower ends were pressed with glass plates, followed by polymerization as in the above 2. The test piece thus prepared was immediately immersed in water at 37° C. for 24 hours before used in the subsequent test.

A color-difference meter, Tokyo Denshoku, Model TC-1, was used to measure lightness of the test piece backed with a standard white board ($L_w$) and lightness of the test piece backed with a standard black board ($L_b$). Transparency was calculated in accordance with the following formula:

$(1-L_b/L_w) \times 100$.

The larger the value, the better the transparency. Values larger than 24 are rated as excellent or E; values of less than 24 up to 20 as Good or G; and value less than 20 as bad or B.

6. Surface gloss and smoothness 0.2 g of a filling composition was cured in a plate form with light irradiation of 20 seconds. The irradiated surface was polished with a White Point (available from Shofu).

The polished surface was observed by the naked eye for smoothness and gloss, and then subjected to measurement of surface roughness, $R_{max}$, in a standard length of 0.25 mm with a surface roughness measuring apparatus, Surfcom 100 A, Tokyo Seimitsu.

7. Particle size and coefficient of standard deviation

Diameters of particles seen in a unit area on photographs of a scanning electron microscope (Di) were measured.

$$\text{Average particle size}(D) = \frac{\sum_{i=1}^{n} Di}{n}$$

$$\text{Coefficient of standard deviation} = \frac{\sigma_{n-1}}{D}$$

wherein $$\sigma_{n-1} = \sqrt{\frac{\sum_{i=1}^{n}(Di - D)^2}{n - 1}}$$

n = number of particles measured.

Examples 1 to 7

Inorganic oxide particles (A) indicated in Table 1 and inorganic oxide particles (B) indicated in Table 2 were mixed with the aforesaid monomer mixture and kneaded to form a pasty filling composition.

The results of the tests are as seen in Table 3.

TABLE 1

| | Particles (A) | |
|---|---|---|
| Type | Average particle size, μm | Coef. of standard deviation |
| A-I | 1.4 | 0.08 |
| A-II | 2.4 | 0.23 |
| A-III | 3.5 | 0.12 |

TABLE 2

| | Particles (B) | |
|---|---|---|
| Type | Particle size range, μm | Content of particles of 0.05 to 0,2 μm, wt. % |
| B-I | 0.05–0.4 | 9 |
| B-II | 0.05–0.4 | 26 |
| B-III | 0.05–0.3 | 28 |
| B-IV | 0.05–0.5 | 32 |
| B-V | 0.05–0.5 | 67 |

TABLE 3

| Example | Weight ratio of particles (A) to (B) | Content of the filler in the composition, wt. % | Compressive strength, kg/cm² | Bending strength, kg/cm² | Knoop hardness number | Water Absorption, mg/cm² | Transparency | Surface Gloss | $R_{max}$ μm |
|---|---|---|---|---|---|---|---|---|---|
| 1 | A-I/B-I = 72/28 | 87 | 3745 | 1825 | 74 | 0.58 | 20.4,G | G | 0.8 |
| 2 | A-I/B-II = 72/28 | 87 | 3807 | 1968 | 75 | 0.57 | 22.2,G | G | 0.7 |
| 3 | A-I/B-III = 65/35 | 88 | 3758 | 1788 | 80 | 0.54 | 24.2,E | G | 0.7 |
| 4 | A-I/B-IV = 64/36 | 85 | 3652 | 1840 | 74 | 0.58 | 24.5,E | G | 0.6 |

TABLE 3-continued

| Example | Weight ratio of particles (A) to (B) | Content of the filler in the composition, wt. % | Compressive strength, kg/cm² | Bending strength, kg/cm² | Knoop hardness, number | Water Absorption, mg/cm² | Transparency | Surface Gloss | R$_{max}$ μm |
| --- | --- | --- | --- | --- | --- | --- | --- | --- | --- |
| 5 | A-I/B-V = 46/54 | 83 | 3733 | 1648 | 72 | 0.61 | 37.2,E | E | 0.3 |
| 6 | A-II/B-II = 72/28 | 84 | 3654 | 1786 | 73 | 0.63 | 21.6,G | G | 0.9 |
| 7 | A-III/B-III = 72/28 | 86 | 3703 | 1850 | 76 | 0.57 | 20.2,G | G | 1.2 |

Comparison Examples 1 to 11

Particles (C) indicated in Tale 4 were used as well as the aforesaid particles (A) and (B). Particles (C-I), (C-II), (C-VI) and C(VII) were surface treated as mentioned above in relation to particles (A) and (B). The particle size ranges of particles (C-III), (C-IV) and (C-V) were determined as mentioned above. The average particle sizes of the other particles (C) were given from the source.

Filling compositions were prepared and tested as in Examples 1 to 7. The results are as shown in Table 5.

TABLE 4

| | | Particles (C) | |
| --- | --- | --- | --- |
| Source and shape | Type | Particles size, μm | Content of particles of 0.05–0.2 μm, wt. % |
| Nippon Aerosil, spherical silica | C-I | average 0.04 | unknown |
| | C-II | average 0.016 | 0 |
| Mitsubishi Kasei, Spherical silica | C-III | range 0.26–0.40 | 0 |
| | C-IV | range 0.08–0.16 | 100 |
| | C-V | range 0.05–0.4 | 3 |
| Tatsumori, Irregular shape silica | C-VI | average 7.0 | trace |
| Fukushima Yogyo, irregular shape quartz | C-VII | average 3.8 | trace | sized silica particles B-VI (available from Mitsubishi Kasei) which were in a particle size range of 0.05 to 0.4 μm and contained 30% by weight of particles in a particle size range of 0.05 to 0.2 μm, and whose part falling in the particle size range of 0.05 to 0.2 μm had an average particle size of 0.12 μm, and the remaining part falling in the particle size range of 0.2 to 0.4 μm had 0.35 μm. Particles (A-1) and particles (B-VI) were premixed in a weight ratio of 62 to 38 in a jet mill type pneumatic mixer. The pre-mixed particles were surface treated as in the above Examples and used together with the aforesaid monomer mixture to prepare a dental filling composition. The content of the filler in the whole composition was 87% by weight. The dental filling composition was tested as in the above Examples to obtain the following results:

| | |
| --- | --- |
| compressive strength | 3,782 kg/cm², |
| bending strength | 1,749 kg/cm², |
| Knoop hardness number | 78, |
| water absorption | 0.56 mg/cm² |
| transparency | 25.6, i.e., excellent, and |
| surface gloss and smoothness | good |
| Rmax | 0.6 μm. |

Example 9

The following two types of spherical zirconia-silica particles (zirconia content 12.5 wt. %) were prepared

TABLE 5

| Comparison Example | Weight ratio of particles (A) to (B) or (C) | Content of the filler in the composition, wt. % | Compressive strength, kg/cm² | Bending strength, kg/cm² | Knoop hardness, number | Water Absorption, mg/cm² | Transparency | Surface Gloss | R$_{max}$ μm |
| --- | --- | --- | --- | --- | --- | --- | --- | --- | --- |
| 1 | A-I/C-III = 72/28 | 87 | 3890 | 1797 | 74 | 0.58 | 18.8,B | G | 0.7 |
| 2 | A-I/C-IV = 72/28 | 78 | 3677 | 1693 | 51 | 0.98 | 31.5,E | G | 0.6 |
| 3 | A-I/C-V = 60/40 | 83 | 3650 | 1662 | 70 | 0.63 | 19.0,B | G | 0.7 |
| 4 | A-I/C-I = 73/27 | 75 | 3480 | 1647 | 48 | 1.02 | 20.2,G | E | 0.3 |
| 5 | A-I/C-II = 62/38 | 64 | 3273 | 1682 | 43 | 1.63 | 24.3,E | E | 0.2 |
| 6 | A-I 100 | 67 | 3445 | 1291 | 46 | 1.48 | 10.3,B | G | 0.9 |
| 7 | B-I 100 | 68 | 3538 | 1036 | 45 | 1.37 | 25.7,E | E | 0.1 |
| 8 | A-I/B-II = 90/10 | 80 | 3607 | 1433 | 66 | 0.72 | 16.8,B | G | 0.9 |
| 9 | A-I/B-II = 10/90 | 75 | 3561 | 1357 | 51 | 0.93 | 38.0,E | E | 0.4 |
| 10 | A-I/C-VI = 72/28 | 83 | 2938 | 1427 | 62 | 0.87 | 17.6,B | B | 4.3 |
| 11 | A-I/C-VII = 65/35 | 85 | 3682 | 1728 | 78 | 0.55 | 12.4,B | B | 3.7 |

As seen from Tables 3 and 5, the cured filling compositions in the Examples showed high compressive strength, high bending strength, and high Knoop hardness number, compared to the cured compositions of the Comparison Examples. They also had low water absorption, good surface gloss and smoothness and excellent transparency though the content of the filler was as high as 80% by weight or more. Thus, the filling composition of the invention is well-balanced among strength, surface gloss and smoothness and transparency.

Example 8

Used were the aforesaid silica particles A-I which had not yet been surface treated and spherical synthe- by hydrolytic polymerization of tetraethylsilicate with tetrabutylzirconate:

Particles (A-IV), average particle size 2.3 μm

Particles (B-VIII), particle size range 0.05 to 0.5 μm; content of particles falling in a range of 0.05 to 0.2 μm, 26 wt. %.

Particles (A-IV) and particles (B-VII) were premixed in a weight ratio of 72 to 28 as in Example 8 and used to prepare a dental filling composition. The content of the filler in the whole composition was 86% by weight. The physical properties of the dental filling composition thus obtained were as follows:

| | |
| --- | --- |
| compressive strength | 3,630 kg/cm², |

-continued

| | |
|---|---|
| bending strength | 1,545 kg/cm², |
| Knoop hardness number | 73, |
| water absorption | 0.64 mg/cm² |
| transparency | 31.5, i.e., excellent, and |
| surface gloss and smoothness | good |
| $R_{max}$ | 0.8 μm. |

Example 10

The spherical zirconia-silica particles (A-IV) mentioned in Example 9 and the spherical synthesized silica particles (B-VI) mentioned in Example 8 were premixed in a weight ratio of 68 to 32 as in Example 8 and used to prepare a dental filling composition. The content of the filler in the whole composition was 87% by weight. The physical properties of the dental filling composition thus obtained were as follows:

| | |
|---|---|
| compressive strength | 3,820 kg/cm², |
| bending strength | 1,688 kg/cm², |
| Knoop hardness number | 76, |
| water absorption | 0.59 mg/cm² |
| transparency | 29.4, i.e., excellent, and |
| surface gloss and smoothness | good |

-continued

| | |
|---|---|
| $R_{max}$ | 0.7 μm. |

We claim:

1. A dental filling composition comprising a polymerizable monomer and an inorganic filler, characterized in that the inorganic filler comprises
   (A) 50% to 75% by weight of spherical inorganic oxide particles with an average particle size of from 1.0 to 3.0 μm, and
   (B) 50% to 25% by weight of spherical inorganic oxide particles which have a particle size range of 0.05 μm to 0.5 μm and 20% to 50% by weight of which is in a particle size range of from 0.05 to 0.2 μm,
   and the total content of the inorganic particles (A) and (B) is at least 80% by weight based on the whole filling composition.

2. The dental filling composition as claimed in claim 1, wherein particles (A) has a coefficient of standard deviation of 0.50 or less.

3. The dental filling composition as set forth in claim 1 wherein the inorganic filler is a pre-mixture of particles (A) and (B) which is to be mixed with the monomer.

* * * * *